United States Patent [19]

Broecker et al.

[11] 3,941,721

[45] Mar. 2, 1976

[54] CATALYST FOR THE MANUFACTURE OF GASES CONTAINING METHANE

[75] Inventors: Franz Josef Broecker; Guenter Zirker; Bruno Triebskorn; Laszlo Marosi, all of Ludwigshafen; Matthias Schwarzmann, Limburgerhof; Winfried Dethlefsen, Ludwigshafen; Knut Kaempfer, Frankenthal, all of Germany

[73] Assignee: BASF Aktiengesellschaft, Ludwigshafen (Rhine), Germany

[22] Filed: Nov. 13, 1973

[21] Appl. No.: 415,407

[30] Foreign Application Priority Data
Nov. 15, 1975 Germany............................ 2255909

[52] U.S. Cl............................ 252/466 J; 260/676 R
[51] Int. Cl.² ...................... B01J 21/04; B01J 23/74
[58] Field of Search ................................ 252/466 J

[56] References Cited

UNITED STATES PATENTS 3,407,149 10/1968 Taylor et al...................... 252/466 J
3,433,610 3/1969 Feldkirchner et al............ 252/466 J

*Primary Examiner*—W. J. Shine
*Attorney, Agent, or Firm*—Johnston, Keil, Thompson & Shurtleff

[57] ABSTRACT

The compound $Ni_6Al_2(OH)_{16} \cdot CO_3 \cdot 4H_2O$ is isolated from aqueous solution. The catalyst is obtained from this compound by drying, calcination and subsequent reduction in a stream of hydrogen, whilst maintaining very specific temperature gradients between the drying stage and the calcination stage. A process for the manufacture of gases containing methane from hydrocarbons by steam cracking, in which the abovementioned catalyst is employed, is also described.

4 Claims, 1 Drawing Figure

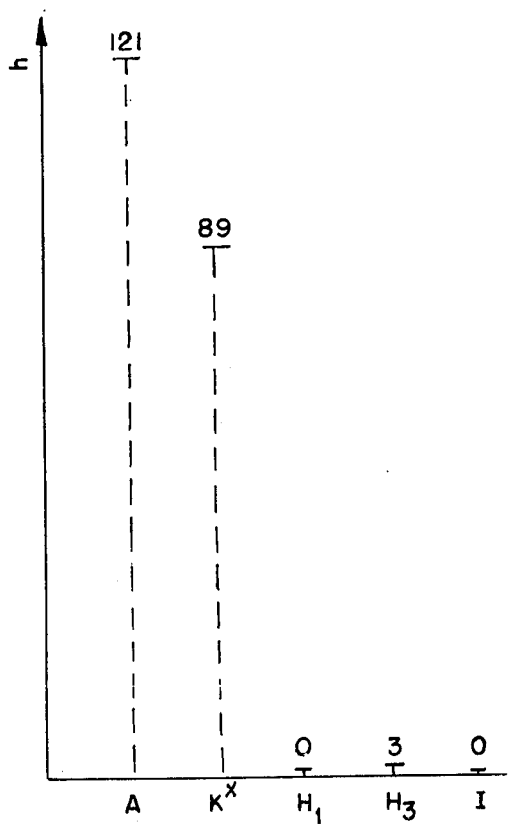

CATALYST FOR THE MANUFACTURE OF GASES CONTAINING METHANE

The invention relates to catalysts which have been obtained by drying, calcination and reduction of specific compounds, the so-called catalyst precursors, produced in aqueous solution, or by precipitation of the catalyst precursors on supports suspended in the aqueous phase, and to the use of these catalysts for the manufacture of gases containing methane by cracking hydrocarbons.

The industrial cracking of preferably gaseous hydrocarbons such as, for example, methane, ethane, propane or butane on nickel catalysts in the presence of steam, to give gases essentially containing carbon monoxide and hydrogen (so-called synthesis gases) has been known for a long time. It is generally carried out at temperatures from 600° to 900°C. This reaction is referred to as steam reforming.

However, hydrocarbons can also be cracked by means of nickel catalysts at lower temperatures to give gases rich in methane. The production of methane-rich gases from hydrocarbons such as ethane, propane, butane or naphtha and the like, at low temperatures, is, however, an exothermic process, in contrast to steam reforming; hence, this reaction is carried out adiabatically in shaft furnaces whilst synthesis gases are manufactured by steam reforming in tubular reactors.

German Printed application No. 1,180,481 discloses that liquid hydrocarbons can be converted into gases rich in methane (containing more than 50% of methane after drying) by means of steam on supported nickel catalysts, at temperatures from 400° to 550°C, provided certain ratios of steam to hydrocarbon are maintained during the reaction.

Conventional supported nickel catalysts are proposed, quite generally, for this process. However, it has been found that the nickel catalysts known from steam reforming at high temperatures are unsuitable for cracking hydrocarbons at low temperatures since their activity is in general inadequate because their supports have in most cases been calcined at high temperatures in order to meet the steam reforming requirements.

The alkali-free catalyst, containing 15% of nickel on aluminum oxide, which the abovementioned German Printed application states to be preferred (cf. column 4, lines 29 to 49) is also rather unsuitable for the process since, if such a catalyst is to have a working life of somewhat more than 14 days, the maximum space velocities permissible are 0.5 kg of hydrocarbon per liter of catalyst. On the other hand, such a process is uneconomical unless space velocities of about 1 to 1.5 kg of hydrocarbon per liter of catalyst per hour are permissible (see comparative experiment in Examples 8 and 9).

German Printed application No. 1,227,603, by the same applicant company, states that the catalyst life in the process described in British Patent No. 820,257 — which is equivalent to the abovementioned DAS 1,180,481 — is relatively short, particularly if higher-boiling hydrocarbons from the boiling range of gasoline are to be cracked.

The abovementioned German Printed application No. 1,227,603, proposes a supported nickel catalyst which contains, in addition to nickel and aluminum oxide, 0.75 to 8.6% of oxides, hydroxides and carbonates of alkali metals or alkaline earth metals, including magnesium. Column 2, from line 44 onward, and column 3, up to line 16, state that optimum results are achieved when alkali metals, especially potassium, are used as catalyst additives. Potassium compounds were therefore used as alkalizing agents in all the examples.

The obligatory alkalization of nickel catalysts before they are used for the steam reforming of, in particular, liquid hydrocarbons in the temperature range from 350° to 1,000°C, that is to say both for the actual steam reforming process and for the production of methane-rich gases, has also been proposed in ICI's German Printed application No. 1,199,427.

In the light of the art, as described above, it was obvious to those skilled in the art to use catalysts containing alkali for the cracking of hydrocarbons since it was generally assumed that only if nickel catalysts containing alkali were used was it possible to prevent the deposition of carbon on the catalyst for acceptable periods of time when carrying out the reaction under economically acceptable conditions — low values of the ratio $(H_2O)/(C)$.

Hence, because of the statements in German Printed application No. 1,227,603 those skilled in the art were prejudiced against the use of the alkali-free nickel catalysts for the production of rich gases since, on the one hand, the promoter action of alkalis such as, for example, potassium, was proven whilst, on the other hand, only a negative result was to be expected from the use of aluminum oxide as the support (cf. Example 9 and the comparative experiments in Example 11 of the present application).

We have found, surprisingly, that alkali-free catalysts containing nickel and aluminium oxide can be manufactured which are superior — for the production of gases containing methane — to those known from the art, if the new catalysts are manufactured from specific catalyst precursors and the latter are converted into the actual catalyst by precipitation, drying, calcination and reduction.

The present invention therefore relates to a catalyst which is characterized in that the compound $Ni_6Al_2(OH)_{16}\cdot CO_3\cdot 4H_2O$ is produced, from aqueous solution, as the catalyst precursor and this compound is converted by drying at temperatures from 80° to 180°C, calcination at temperatures from 300° to 550°C and subsequent reduction in a stream of hydrogen, into the actual catalyst, with the provise that between the drying stage and the calcination stage the temperature is raised at a gradient in the range from 1.66°C/minute to 3.33°C/minute.

The invention further relates to the use of this catalyst for the production of gases containing methane; and in particular gases rich in methane, by cracking hydrocarbons of 2 to 30 C atoms, corresponding to a boiling range from 30° to 300°C, in the presence of steam.

Hence, the invention is further characterized by the use of the catalyst for the manufacture of gases containing methane from hydrocarbons of 2 to 30 C atoms or their mixtures, in which process the hydrocarbon vapors and steam are passed through the catalyst bed under atmospheric pressure or superatmospheric pressures at rates of 1 to 2 kg of hydrocarbon per liter of catalyst per hour and at temperatures above 250°C, and the catalyst is kept at temperatures from 300° to 550°C by the heat liberated in the reaction which takes place.

As already described in the introduction, this reaction is exothermic and can therefore be performed adiabatically in a shaft furnace if the reactants have been preheated to a sufficiently high temperature. In the case of prior art catalysts this process was generally performed by preheating the feedstocks to temperatures exceeding 350°C and passing them into the catalyst bed in such a way that the bed was kept at temperatures from 400° to approx. 550°C as a result of the reaction which occurs (cf. DAS No. 1,180,481 and DAS No. 1,227,603).

The catalysts of the invention make it possible to perform the abovementioned process adiabatically at lower temperatures. This means that the hydrocarbon feedstocks need be heated to less high temperatures; preheating to temperatures of 250°C even suffices. If the reaction is carried out adiabatically, the cracking can therefore be effected at temperatures from 250° to 550°C though preferably the process is performed at temperatures from 300° to 450°C and especially from 300° to 400°C. The above data relate to the temperature to which the steam/hydrocarbon mixture is preheated. This temperature depends on the feedstock used and can be the lower, the lower-boiling is the hydrocarbon mixture and the higher is the proportion of paraffin in this hydrocarbon mixture.

It is known that the equilibrium of the reaction, and hence the methane content in the gas, greatly depends on the temperature and pressure; it is the higher, the lower is the selected reaction temperature and the higher is the selected pressure.

It is therefore advantageous that the catalysts according to the invention can be used at pressures from 10 to 100 atmospheres gauge; preferably, pressures from 25 to 85 atmospheres gauge are chosen.

The feedstocks which can be used are hydrocarbons of higher molecular weight than methane. Mixtures of hydrocarbons of average C number from $C_2$ to $C_{30}$, corresponding to a boiling range from about 30° to 300°C, are preferred. Hydrocarbon mixtures consisting predominantly of paraffinic hydrocarbons are particularly suitable. The proportion of paraffinic hydrocarbons in the mixture should be not less than 70 percent by volume.

The feedstock (naphtha) should be desulfurized to sulfur contents below 0.5 ppm since the prior art nickel catalysts, like the catalysts of the invention, do not stand up well to higher sulfur contents for a prolonged period. This poisoning is a feature shown by all nickel cracking catalysts, so that as a matter of principle the feedstock must be thoroughly desulfurized before being employed for cracking. This desulfurization is known in the art and is usually effected with sulfur-resistant catalysts.

The catalysts of the invention can be exposed to 1.0–2.5 kg of naphtha/liter of catalyst per hour; preferably, space velocities of 1.2 to 1.5 kg of naphtha/liter of catalyst per hour are used for industrial installations. In comparative experiments, a space velocity of 5 kg of naphtha/liter of catalyst per hour was employed (compare Example 11) in order to be able to achieve appropriate effects within acceptable periods of time. The abovementioned space velocity is not relevant to the industrial cracking of liquid hydrocarbons. However, the catalyst of the invention is capable of reliably splitting petroleum fractions of upper boiling limits extending to 300°C at space velocities of up to 2 kg of naphtha/liter of catalyst. In the case of gasolines whose upper boiling limits are lower, higher space velocities than 2 can be employed. When cracking propane or butane, space velocities of up to 3.5 kg of naphtha/liter of catalyst per hour can be employed. These data shown that the space velocity depends on the hydrocarbon used.

The weight ratio of steam/naphtha should be not less than 0.8. For steam reforming using the catalyst of the invention, ratios from 1.0 to 2.0 kg of steam per kg of naphtha are used. The use of higher ratios is not critical but is uneconomical. The amount of steam required depends on the nature of the feedstock; the ratio chosen can be lower when low-boiling hydrocarbons are used, especially if the hydrocarbons to be cracked are predominantly paraffinic.

Preferably, 1 M to 2 M aqueous solutions of the nitrates are used to produce the catalyst precursor $Ni_6Al_2(OH)_{16}.CO_3.4H_2O$. The precipitant (alkali metal carbonate) is also preferably used as a 1 M to 2 M solution. The following method has been found suitable for the production of a catalyst precursor of the abovementioned composition:

The compound $Ni_6Al_2(OH)_{16}.CO_3.4H_2O$ is precipitated with alkali metal carbonates (sodium carbonate or potassium carbonate or mixtures of both) at pH values from 6.5 to 10.5, especially from 7.0 to 8.5. The starting material is an aqueous solution of the nitrates of the divalent and trivalent metals, the pH of which has been adjusted to 8 with sodium carbonate. The molar ratio $Me^{2+}:Me^{3+}$ in this solution should at least exceed 1 but should preferably be from 2.5 to 3.5; in particular, a value of 3:1 (the stoichiometric value) is chosen for the ratio of $Me^{2+}:Me^{3+}$.

The catalyst precursor can be precipitated at temperatures from 0° to 100°C but preferably the precipitation is effected at temperatures from 70° to 90°C. Preferably, the catalyst precursor is produced by adding 2 M solutions of the alkali metal carbonates to 2 M mixtures of the nitrates. The precipitate formed is carefully washed until its residual alkali content is less than 0.1 or less than 0.01 percent, based on the dry catalyst precursor. The resulting compounds, when dried, calcined and reduced in a stream of hydrogen, give catalysts superior to those known from the art (cf. in particular, Example 11).

The subsequent treatment stages, such as drying, calcination and the use of a certain rate of heating between the drying stage and the calcination stage, are as important as the observance of certain precipitation conditions, such as the pH value and careful removal of alkalis to values below 0.1 percent or values below 0.01 percent; hence, the essential aspects of the invention are the manufacture of the individual alkali-free catalyst precursor, its drying and the defined temperature rise, at a rate from 1.66° to 3.33°C/minute, between drying and subsequent calcination.

The subsequent reduction of the catalyst is in general effected in a stream of hydrogen at temperatures from 300° to 500°C.

The catalyst precursor is dried in a narrow temperature range, from 80° to 180°, the range from 90° to 120°C being particularly preferred. The drying can be effected in air.

The dried catalyst precursor is calcined at temperatures from 300° to 550°C. Temperatures from 340° to 460°C are preferred.

Between the drying stage and the calcination stage, the substance should be heated at a definite rate which is as rapid as possible. The time for heating from the preferred drying temperature (90° to 210°C) to the preferred calcination temperature range (340° to 460°) should be not less than 1.5 hours but no more than 3 hours. From this, the said gradients for the temperature rise are calculated to be from 1.66°C/minute to 3.33°C/minute.

The nickel content of the catalyst produced directly from the catalyst precursor can, of course, not be varied within wide limits since it is essentially determined by the stoichiometry of the catalyst precursor. After reduction of the catalyst, the nickel contents are of the order of magnitude of 72 to 80 percent, preferably about 77.5%.

These values apply to a catalyst produced directly from the catalyst precursor.

However, the catalyst precursor can also be precipitated on ceramic supports, such as aluminum oxide, hydrated alumina (bayerite, boehmite, hydrargillite or their mixtures), titanium oxide, silica, zirconium dioxide and artificial and synthetic silicates, such as magnesium silicate or aluminosilicates.

This precipitation is preferably effected by having the support in the form of an aqueous suspension and precipitating the catalyst precursor onto it. The support and precipitate are separated off and treated further in the way described for the conversion of the catalyst precursor.

Hydrated aluminas are preferred supports (cf. Examples 2 and 3). Their use makes it possible to obtain any desired nickel content in the finished catalyst. In general, nickel contents from 15 to 77.5 percent by weight are chosen.

The use of the catalysts of the invention is particularly preferred, in industry, for the production of gases containing methane and for the after-treatment of the rich gases produced by naphtha cracking, with the object of producing substitute gases for natural gas (the so-called post-methanization of methane-rich gases). In multi-stage processes for the production of substitute gases for natural gas the catalysts according to the invention can be used with particular advantage both in the cracking stage and in the postmethanization stages.

The manufacture of the catalysts of the invention is described in more detail in Examples 1, 2 and 3 which follow. Example 4 describes the use of the catalysts in cracking hydrocarbons to produce gases containing methane. Examples 6 and 7 relate to the post-methanization of the rich gases, produced in a 1st process stage, in a further catalytic process stage. Example 5 describes how a refinery gas containing carbon monoxide and dioxide can be converted into a gas rich in methane, using the catalysts according to the invention.

Example 11 compares the catalyst A of the invention with the catalysts from the art according to DAS No. 1,180,481 ($H_1$ and $H_3$) in respect of their performance in the production of gases containing methane. These experiments provide impressive evidence that the alkali-free catalysts according to the invention are of substantially greater activity than those according to the prior art, especially at high space velocities, such as are used nowadays in industry. Example 11 also shows that the catalyst (A) according to the invention is superior in all respects to the alkalized contact catalysts from the state of the art (cf. K) according to DAS No. 1,227,603. In particular, its capacity for higher space velocities, and the associated longer life of the catalyst of the invention as compared to the alkalized nickel catalysts used in industry, should be singled out. When the catalysts are used to produce gases containing methane, this increased activity of the catalysts of the invention has the advantage that the process can be carried out at lower temperatures so that methane contents from 65 to 75 percent by volume can be achieved even in one process stage, and these products can then be converted, in only one further catalytic process stage, with subsequent drying and a $CO_2$ wash, into gases which can be used as substitute gases for natural gas and which conform to the specifications laid down for these gases (sum of $H_2 + CO$ at most 0.1 percent by volume, based on the gas after the $CO_2$ wash).

When producing methane, the cracked gases can be cooled, after the first catalytic process stage, to temperatues below the reactor exit temperature in order to condense out the excess water; temperatures below 100°C, for example temperatures in the range of 20° to 80°C, are preferably chosen for this purpose (dry methanization).

However, it is also possible to remove only part of the water from the cracked gases after the first catalytic process stage and to convert the cracked gases, which still contain water, direct into gases rich in methane in a further catalytic stage ("wet methanization", cf. Examples 6 and 7).

Gases containing carbon monoxide and dioxide are used as feedstocks for the reaction in the second catalytic stage of the process; the rich gases obtained from the low temperature cracking of naphtha, which can in general contain 50 to 75% of methane, 19 to 25% of carbon dioxide, up to 16% of hydrogen and up to 5% of carbon monoxide, are particularly suitable. We have found that these dry gases can be passed into the bed of the nickel catalyst, using preheat temperatures from 200° to 300°C, without causing coking of the catalyst. This was surprising since German Published application No. 1,645,840 alleges that the post-methanization of rich gases can only be carried out in the presence of water because the nickel catalysts used for the methanization tend to coke in the absence of water.

Space velocities from 2,000 to 10,000 l (S.T.P.) of gas per liter of catalyst per hour can be chosen for the second catalytic treatment stage. The space velocities chosen are lower for higher carbon monoxide contents of the cracked gases whilst conversely somewhat higher space velocities can be selected at low carbon monoxide contents of the feedstock. Space velocities from 3,000 to 7,000 l (S.T.P.) of gas per liter of catalyst per hour are preferred.

EXAMPLE 1

Catalyst A

To precipitate the compound $Ni_6Al_2(OH)_{16}CO_3 \cdot 4H_2O$, which serves as the catalyst precursor, the following 2 M solutions were prepared first:

Solution 1

13.960 kg = 48 moles of $Ni(NO_3)_2 \cdot 6H_2O$ and
6.002 kg = 16 moles of $Al(NO_3)_3 \cdot 9H_2O$
were dissolved in sufficient water to produce a total of 32 l of solution.

Solution 2

7.635 kg = 72 moles of sodium carbonate were also dissolved in water and made up to 36 l.

10 l of water were introduced into a stirred kettle. During the precipitation, the pH was measured with an electrode which dipped into the water introduced. Both the above solutions, and the water introduced, were separately heated to 80°C. The pH of the water introduced was adjusted to 8.0 by adding a suitable amount of solution 2.

To precipitate the above compound, solutions 1 and 2 were allowed to run separately into the water and a pH value of 7.5 to 8.0 was maintained by regulating the rate of addition, whilst stirring well. After the whole of solution 1 had been added the addition of solution 2 was stopped and the precipitate was stirred for a further 15 minutes at 80°C. The resulting precipitate was filtered off and washed until free of alkali. The washed product, which according to X-ray tests proved to be a pure precipitate of $Ni_6Al_2(OH)_{16}CO_3 \cdot 4H_2O$ was then dried for 24 hours at 110°C, calcined for 20 hours at 450°C, mixed with 2% of graphite and pressed to give 5 × 5 mm pills. Analysis showed the following constituents (all the data being in per cent by weight, and based on the oxide contact catalyst): nickel 56.8%, aluminum 9.5% and sodium 0.009%.

EXAMPLE 2

Catalyst B

The catalyst B contains a hydrated alumina ss the support. This hydrated alumina was obtained by parallel precipitation of sodium aluminate solution and nitric acid within the pH range of 7.5 to 8.0. The precipitate was filtered off, washed until free of alkali and then dried at 200°C.

3,720 kg of this support were suspended in 10 l of water in a stirred kettle and the suspension was heated to 80°C. The compound $Ni_6Al_2(OH)_{16}CO_3 \cdot 4H_2O$ was now precipitated on this suspended support. For this purpose, two solutions were prepared and separately heated to 80°C.

Solution 1
 13.960 kg = 48 moles of $Ni(NO_3)_2 \cdot 6H_2O$ and
 6.002 kg = 16 moles of $Al(NO_3)_3 \cdot 9H_2O$
were dissolved in water and made up to 32 l of solution.

Solution 2
 7.635 kg of technical grade sodium carbonate were dissolved in water and made up to 36 l of solution.

The compound $Ni_6Al_2(OH)_{16}CO_3 \cdot 4H_2O$ was then precipitated onto the hydrated alumina (namely the support) at pH 7.5 to 8.0, as described in Example 1. The precipitated product was stirred for a further 15 minutes and the precipitate was then filtered off, washed until free of alkali, dried at 110°C, calcined for 20 hours at 450°C, mixed with 2% of graphite and finally pressed to give 5 × 5 mm pills. Analysis showed that the oxide contact catalyst contained: 39.3% of nickel, 24.1% of aluminum, 0.01% of sodium (all data being in percent by weight).

Catalyst C

This catalyst was prepared as described above except that the compound $Ni_6Al_2(OH)_{16}CO_3 \cdot 4H_2O$ was precipitated on 4.080 kg of the suspended support and the dry precipitate was calcined at 350°C. The resulting (oxide) catalyst contained: 32.5% of nickel, 27.1% of aluminum and 0.009% of sodium (all data being in percent by weight).

Catalyst D

This catalyst was prepared like catalyst C, except that the amount of hydrated alumina used to start with was modified. A supported catalyst containing: 16.7% of nickel, 38.3% of aluminum and 0.007% of sodium (all data being in percent by weight) was obtained.

Catalyst E

This catalyst was prepared like catalyst C and D, except that the compound $Ni_6Al_2(OH)_{16}CO_3 \cdot 4H_2O$ was precipitated on 6.830 kg of suspended hydrated alumina. The resulting catalyst, in the oxide state, contained: 23.9% of nickel, 31.4% of aluminum and 0.01% of sodium (all data being in percent by weight).

EXAMPLE 3

Catalyst F

A hydrated alumina support was prepared by parallel precipitation of an aluminum sulfate solution with ammonia at pH 7.5. The precipitate was filtered off, washed until the sulfate content fell below 0.5% by weight, and dried at 200°C.

0.134 kg of this carrier were suspended in 10 l of water in a stirred kettle. The compound $Ni_6Al_2(OH)_{16}CO_3 \cdot 4H_2O$ was precipitated on the hydrated alumina as described in Example 2. The precipitate was filtered off, washed, dried at 110°C, calcined for 20 hours at 350°C and finally pressed to give 5 × 5 mm pills. A catalyst containing 52.4% of nickel, 12.2% of aluminum, 0.006% of sodium (all data being in percent by weight) was obtained.

Catalyst G

This catalyst was prepared like catalyst F except that 4.080 kg of hydrated alumina were taken initially. The catalyst contained 33.1% of nickel, 26.7% of aluminum and 0.008% of sodium (all data being in percent by weight and based on the product as oxide).

EXAMPLE 4

Catalyst A 200 ml of catalyst A were reduced with hydrogen at 450°C under a pressure of 16 atmospheres absolute, in a reaction tube of 24 mm internal diameter, which could be heated externally by means of an aluminum block.

A desulfurized naphtha (density: 0.727 g/cm³, boiling range 80° to 155°C) was vaporized, 2 kg of water being added per 1 kg of naphtha, and the vapor was passed through the catalyst under a pressure of 30 atmospheres absolute and at an entry temperature of 380°C. The space velocity was 5 kg of naphtha per liter of catalyst per hour. The temperature of the surrounding aluminum block was kept at 450°C. On cooling the cracked gas issuing at 462°C from the catalyst layer, the hourly yield was 1.31 kg of water and 1,770 l (S.T.P.) of a dry gas which consisted of 65.9 percent by volume of methane, 32.1 percent by volume of carbon dioxide, 10.6 percent by volume of hydrogen and 0.4 percent by volume of carbon monoxide.

Catalyst B

Using catalyst B, with the same feedstock and under the conditions stated above, a cracked gas issuing from the catalyst bed at a temperature of 470°C was obtained. On cooling the cracked gas, the hourly yield was 1.31 kg of water and 1,680 l (S.T.P.) of a dry gas which consisted of 64.8% of methane, 23.0% of carbon dioxide, 11.7% of hydrogen and 0.5% of carbon monoxide (all data being in percent by volume).

Catalyst F

Catalyst F was employed for the cracking of naphtha under the same conditions as catalysts A and B. On cooling the cracked gas, which issued at 468°C from the catalyst bed, the hourly yield was 1.30 kg of water and 1,750 l (S.T.P.) of a dry gas which consisted of 65.0% of methane, 23.1% of carbon dioxide, 11.4% of hydrogen and 0.5% of carbon monoxide (all data being in percent by volume).

EXAMPLE 5

Catalyst C 200 ml of catalyst C were reduced with hydrogen at 400°C and under a pressure of 16 atmospheres absolute in a tubular reactor of 24 mm internal diameter which could be heated externally by means of an aluminum block.

A dry gas consisting of: 60.5% of methane, 25.9% of hydrogen, 12.5% of carbon dioxide and 1.1% of carbon monoxide (all data being in percent by volume), was withdrawn from a pressure vessel, heated and mixed with steam in the ratio of 1.07 moles of $H_2O$ per 1 mole of dry gas. The wet gas thus produced, the composition of which corresponds to a cracked gas produced by catalytic steam reforming of a refinery gas, was passed through the catalyst at a pressure of 17 atmospheres absolute and an entry temperature of 270°C, using a space velocity of 6,020 l (S.T.P.) of wet gas per liter of catalyst per hour. The temperature of the surrounding aluminum block was kept at 270°C. On cooling the wet gas issuing from the catalyst bed at 295°C, the hourly yield was 0.56 liter of water and 450 l (S.T.P.) of a dry gas which consisted of 85.5% of methane, 4.3% of hydrogen, 10.2% of carbon dioxide and less than 0.05% of carbon monoxide (all data being in percent by volume).

Catalyst D

Catalyst D was employed, under the same conditions as those described for catalyst C, for the post-methanization of a refinery cracked gas containing carbon monoxide and carbon dioxide.

On cooling the wet gas issuing at 300°C from the catalyst bed, the hourly yield was 0.56 liter of water and 450 l (S.T.P.) of a dry gas which consisted of 84.9% of methane, 5.0% of hydrogen, 10.1% of carbon dioxide and less than 0.05% of carbon monoxide (all data being in percent by volume).

EXAMPLE 6

450 ml of catalyst A were reduced with hydrogen at 450°C under a pressure of 16 atmospheres absolute in a tubular reactor of 24 mm internal diameter which could be heated externally by means of an aluminum block.

A desulfurized naphtha (density: 0.727 g/cm³; boiling range 80° to 155°C) was vaporized, with the addition of 2 kg of water of 1 kg of naphtha and the vapor was passed through the catalyst under a pressure of 30 atmospheres absolute and using an entry temperature of 400°C. The space velocity was 0.9 kg of naphtha per liter of catalyst per hour. The temperature of the surrounding aluminum block was kept at 450°C. On cooling the cracked gas issuing at 455°C from the catalyst bed, the hourly yield was 0.54 kg of water and 700 l (S.T.P.) of a dry gas which consisted of 67.1% of methane, 22.9% of carbon dioxide, 9.6% of hydrogen and 0.4% of carbon monoxide (all data being in percent by volume).

After operating for 24 hours, a second tubular reactor, of 32 mm internal diameter, which could also be heated externally by means of an aluminum block, was connected in series behind the first tubular reactor. This second reactor contained 250 ml of catalyst E which had first been reduced with hydrogen at 350°C under a pressure of 16 atmospheres absolute. The water which condensed out after the first tubular reactor was fed in again before the second reactor, vaporized and mixed with the dry gas from the first reactor. The wet gas thus obtained, (the composition of which corresponds to that of the wet gas issuing from the catalyst bed of the first reactor) was passed through the catalyst E contained in the second reactor under a pressure of 30 atmospheres absolute and using an entry temperature of 270°C. The temperature of the surrounding aluminum block was kept at 270°C. On cooling the gas issuing at 305°C from the catalyst bed, the hourly yield was 0.56 kg of water and 650 l (S.T.P.) of a dry gas which consisted of 75.6% of methane, 22.8% of carbon dioxide, 1.6% of hydrogen and less than 0.05% of carbon monoxide (all data being in percent by volume).

After 1,040 hours, no change in the composition of the gases produced in the first and second tubular reactors was as yet ascertainable. Whilst continuing to crack the naphtha in the first tubular reactor, the catalyst E in the second tubular reactor was now replaced by the catalyst D: 250 ml of catalyst D were reduced and employed for 1,090 hours under the same conditions as was the catalyst E previously. On cooling the gas issuing at 302°C from the catalyst bed, the hourly yield was 0.56 kg of water and 660 l (S.T.P.) of a dry gas which consisted of 74.0% of methane, 22.8% of carbon dioxide, 3.2% of hydrogen and less than 0.05% of carbon monoxide (all data being in percent by volume). Since the composition of the gases produced in the first and second tubular reactors continued unchanged, the experiment was discontinued after 1,220 hours.

EXAMPLE 7

200 ml of catalyst A were reduced as described in Example 6 and employed for the steam reforming of naphtha under conditions identical to those of Example 6 with the exception of the space velocity, which was now 2.0 kg of naphtha per liter of catalyst per hour. On cooling the cracked gas issuing at 475°C from the catalyst bed, the hourly yield was 0.53 kg of water and 710 l (S.T.P.) of a dry gas which consisted of 66.2% of methane, 22.4% of carbon dioxide, 10.9% of hydrogen and 0.5% of carbon monoxide (all data being in percent by volume).

After 24 hours' operation, a second tubular reactor containing 200 ml of catalyst C was connected in series behind the first tubular reactor. The reduction and operation of the catalyst C were effected identically to those described for catalyst E in Example 6. On cooling the gas issuing at 315°C from the catalyst bed, the hourly yield was 0.56 kg of water and 650 l (S.T.P.) of a dry gas which consisted of 75.4% of methane, 22.9% of carbon dioxide, 3.2% of hydrogen and less than 0.05% of carbon monoxide (all data being in percent by volume).

The experiment was discontinued after 520 hours since after this time a change in the composition of the gases produced in the first and second tubular reactors was not yet detectable.

EXAMPLE 8

The comparative experiments were carried out under the conditions indicated in Examples 1 and 2 of German Printed application No. 1,180,481, namely:

| | |
|---|---|
| Catalyst temperature: | 500°C |
| Preheat temperature of the mixture: | 450°C |
| Pressure: | 25 atmospheres |
| Feedstock: | naphtha |
| Steam-naphtha ratio: | 2 kg/kg |
| Space velocity: | 0.5 kg of naphtha/1 of catalyst.hour. |

The naphtha used had a density of 0.693 g/cm$^3$ (at 20°C) and a boiling range of 63° to 102°C. It contained 88 percent by volume of paraffins, 10 percent by volume of naphthenes with 6-membered rings and 2 percent by volume of aromatics. Since the examples do not specify the space velocity, the low velocity indicated above was chosen.

Three commercially available nickel catalysts from BASF, suitable for the high temperature steam reforming of hydrocarbons, and the special catalyst ($H_1$) containing 15% of nickel, described in the cited Printed application, were compared. The table which follows shows the nickel contents, the support of the catalysts mentioned, and the tradenames of the catalysts:

| Type of catalyst | % by weight of nickel | Support |
|---|---|---|
| G 1 - 11 | 6 | Magnesite |
| G 1 - 21 | 16 | Kaolin + magnesium oxide + alumina cement |
| G 1 - 40 | 20 | Magnesium oxide + alumina |
| $H_1$; manufactured according to DAS 1,180,481, column 4, lines 29 et seq. | 15 | Alumina |

The experiments were carried out in a tubular reactor which in each case contained 270 cm$^3$ of the catalysts mentioned.

The results of the experiments are shown in the table which follows:

The experiments show that the process cannot be carried out with the commercially available nickel cracking catalysts since all three catalysts are deactivated very quickly. The experiment with catalyst G1-11 was discontinued after 8 days. When the conversion had fallen to merely 11% by weight, and the experiment with catalyst G1-21 was discontinued after 9 days, at a conversion of 30% by weight. Since the experiment with catalyst G1-40 showed a conversion which was still as much as 61% by weight of the naphtha after 9 days, this experiment was extended to a total of 14 days. After this time, the catalyst was found to be completely deactivated and no longer converted any naphtha. This at the same time shows that the catalyst activity does not stabilize itself and instead the activity decreases until the catalyst has become completely deactivated within a very short time.

These experiments show that nickel catalysts are simply unsuitable for the process described in the cited German Printed application. Only the special nickel catalyst on a pure alumina support, manufactured according to DAS No. 1,180,481, proved suitable to a very limited degree; the experiment with this catalyst was also extended to 14 days. After this time, the catalyst still converted naphtha completely. However, with a commercial space velocity of 1 kg of naphtha per liter of catalyst per hour, this catalyst also no longer permits complete cracking of the naphtha (compare also Example 9).

(With regard to the method used for the experiments, it should be noted that the gas chromatography method was capable of detecting 1 ppm of higher hydrocarbons).

EXAMPLE 9

| | |
|---|---|
| Experimental conditions: | |
| Catalyst temperature (maximum temperature of aluminum block) | 470°C |
| Preheat temperature of the mixture | 420°C |
| Pressure | 30 atmospheres |
| Feedstock | naphtha |

| Duration days | Catalyst G1-11 % by weight of naphtha converted | Catalyst G1-21 % by weight of naphtha converted | Catalyst G1-40 % by weight of naphtha converted | $H_1$; DAS 1,180,481 % by weight of naphtha converted | |
|---|---|---|---|---|---|
| Start | 100.0 | 100.0 | 96.7 | 100 | 100 |
| 1 | 93.4 | 97.9 | 94.0 | | 100 |
| 2 | 82.0 | 82.6 | 93.1 | | 100 |
| 3 | 43.7 | 53.0 | 91.6 | | 100 |
| 4 | — | 36.9 | 76.1 | | 100 |
| 5 | — | 23.3 | 75.0 | | 100 |
| 6 | 30.2 | 15.9 | — | | 100 |
| 7 | 18.8 | 32.7 | 54.5 | | 100 |
| 8 | 10.7 | — | — | | 100 |
| 9 | — | 29.9 | 61.0 | | 100 |
| 10 | — | — | 48.2 | | 100 |
| 12 | — | — | 18.5 | | 100 |
| 14 | — | — | 0 | | 100 |

-continued

Steam/naphtha ratio        2 kg/kg
Space velocity             1 kg of naphtha/1 of
                           catalyst.hour The naphtha used had a density of 0.728 g/cm³ at 20°C and a boiling range of 80° to 150°C. It contained 62% by volume of paraffins, 34.5% by volume of naphthalenes and 3.5% by volume of aromatics.

In these comparative experiments, which were carried out with 200 ml of catalyst in a tubular reactor, lower temperatures, a higher pressure, a higher-boiling naphtha and, in particular, a higher space velocity than in Example 8 were used. The results are shown in the table which follows:

| | Catalyst according to DAS 1,180,481 | Nickel content % by weight | Time at which unchanged naphtha is found in the output |
|---|---|---|---|
| 1 | $H_1$ | 15 | from the start |
| 2 | $H_2$ | 24.9 | from the start |
| 3 | $H_3$ | 51.2 | after 7 hours |

EXAMPLE 10

Catalyst I

A catalyst was produced by precipitation in accordance with the instructions of German Printed application No. 1,227,603. The precipitate was filtered off, suspended 6 times in hot water, alkalized, dried at 110°C and calcined at 450°C. The calcined material was then mixed with 2% of graphite and pressed to give 5 × 5 mm tablets. Analysis of the oxide catalyst showed: 25.0% of nickel, 65.4% of $Al_2O_3$, 3.05% of potassium (all data being in percent by weight).

Catalyst K

The catalyst was prepared analogously to Example 6 of German Printed application No. 1,227,603. The analysis of the oxide catalyst showed: 61.4% of nickel, 19.5% of $Al_2O_3$, 1.31% of potassium (all data being in percent by weight).

EXAMPLE 11

To compare the activity of catalysts $H_1$, $H_3$, I, K and A, all were tested under the following conditions:

The experiments were carried out in the same tubular reactor, which had an internal width of 24 mm and was surrounded by an aluminum block. The naphtha-steam mixture entered at 380°C. A desulfurized naphtha of density 0.727 g/cm³ and boiling range 80° to 155°C was employed. The space velocity was 5 kg of naphtha per liter of catalyst per hour, using a weight ratio of $H_2O$/hydrocarbon = 2.0 and a pressure of 30 atmospheres absolute. The temperature of the surrounding aluminum block was 450°C.

The parameter measured in order to compare the activity was the time in hours after which quantities of unconverted higher hydrocarbons first occured in the cracked gas. Results are shown in the table and represented in the FIGURE.

| Catalyst | % by weight of Ni in oxide catalyst | % by weight of K or Na in oxide catalyst | Naphtha slip |
|---|---|---|---|
| $H_1$ | 15.2 | 0.01 | from the start |
| $H_3$ | 51.2 | 0.01 | after 3 hours |
| I | 25.0 | 3.05 | from the start |
| K | 61.4 | 1.31 | after 89 hours |
| A (Example 1) | 56.8 | 0.009 | after 121 hours |

We claim:

1. A catalyst produced by the process consisting essentially of precipitating the compound $Ni_6Al_2(OH)_{16}\cdot CO_3\cdot 4H_2O$ as a catalyst precursor from an aqueous medium; drying said precipitate at a temperature of from 80° to 180°C; raising the temperature of said precipitate between the drying stage and the calcination stage at a gradient of 1.66°C/minute to 3.33°C/minute; calcining said precipitate at a temperature of from 300° to 550°C; and thereafter reducing said precipitate in a stream of hydrogen to form said catalyst.

2. A catalyst produced by the process consisting essentially of precipitating the compound $Ni_6Al_2(OH)_{16}\cdot CO_3\cdot 4H_2O$ on a support as a catalyst precursor from an aqueous medium; drying said precipitate and said support at a temperature of from 80° to 180°C; raising the temperature of said precipitate and said support between the drying stage and the calcination stage at a gradient of 1.66°C/minute to 3.33°C/minute; calcining said precursor at a temperature of from 300° to 550°C; and thereafter reducing said precursor in a stream of hydrogen to form said catalyst.

3. A catalyst produced by a process as set forth in claim 1 wherein the precipitate is dried at a temperature of from 90° to 120°C and is calcined at a temperature of from 340° to 460°C.

4. A catalyst produced by a process as set forth in claim 2 wherein said support is hydrated alumina.

* * * * *